US012672764B2

(12) United States Patent
Yamamoto

(10) Patent No.: US 12,672,764 B2
(45) Date of Patent: Jul. 7, 2026

(54) ENDOSCOPE SYSTEM, PROCESSOR, AND METHOD FOR ESTIMATING TEMPERATURE OF ENDOSCOPE

(71) Applicant: OLYMPUS MEDICAL SYSTEMS CORP., Tokyo (JP)

(72) Inventor: Sayuri Yamamoto, Hino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 303 days.

(21) Appl. No.: 18/244,506

(22) Filed: Sep. 11, 2023

(65) Prior Publication Data

US 2023/0414076 A1      Dec. 28, 2023

Related U.S. Application Data

(63) Continuation of application No. PCT/JP2021/010709, filed on Mar. 16, 2021.

(51) Int. Cl.
*A61B 1/005* (2006.01)
*A61B 1/00* (2006.01)

(52) U.S. Cl.
CPC ........ *A61B 1/0051* (2013.01); *A61B 1/00097* (2022.02); *A61B 1/0058* (2013.01)

(58) Field of Classification Search
CPC ... A61B 1/00097; A61B 1/0058; A61B 1/127; A61B 1/128
See application file for complete search history.

(56) References Cited

U.S. PATENT DOCUMENTS

2009/0299353 A1* 12/2009 Lewinsky .............. A61B 18/28
606/16
2017/0311789 A1* 11/2017 Mulcahey .............. A61B 1/126
2018/0080437 A1    3/2018 Morishima
(Continued)

FOREIGN PATENT DOCUMENTS

JP        2010-187903 A        9/2010
JP            5411086 B2        2/2014
JP            5535305 B2        7/2014
(Continued)

OTHER PUBLICATIONS

International Search Report dated Jun. 15, 2021 received in PCT/JP2021/010709.

*Primary Examiner* — Aaron B Fairchild
(74) *Attorney, Agent, or Firm* — Scully, Scott, Murphy & Presser, P.C.

(57)                      ABSTRACT
An endoscope system includes: an endoscope equipped with an insertion portion inserted into a subject; a heating element provided in the insertion portion and configured to generate heat; a temperature sensor configured to acquire heating element temperature data on temperature of the heating element; and a processor. The processor outputs initial surface temperature, which is data on insertion portion surface temperature at a first time point prior to a heating start time of the heating element, based on the heating element temperature data at the first time point and estimates changes in the insertion portion surface temperature over time after the first time point based on the heating element temperature data after the first time point using the initial surface temperature as an initial value of the insertion portion surface temperature.

5 Claims, 10 Drawing Sheets

(56)                    References Cited

U.S. PATENT DOCUMENTS

2019/0046010 A1     2/2019  Tojo et al.

FOREIGN PATENT DOCUMENTS

| JP | 2020-116147 | A | 8/2020 |
| WO | 2016/189683 | A1 | 12/2016 |
| WO | 2017/179126 | A1 | 10/2017 |
| WO | 2018/189888 | A1 | 10/2018 |

* cited by examiner

FIG. 3

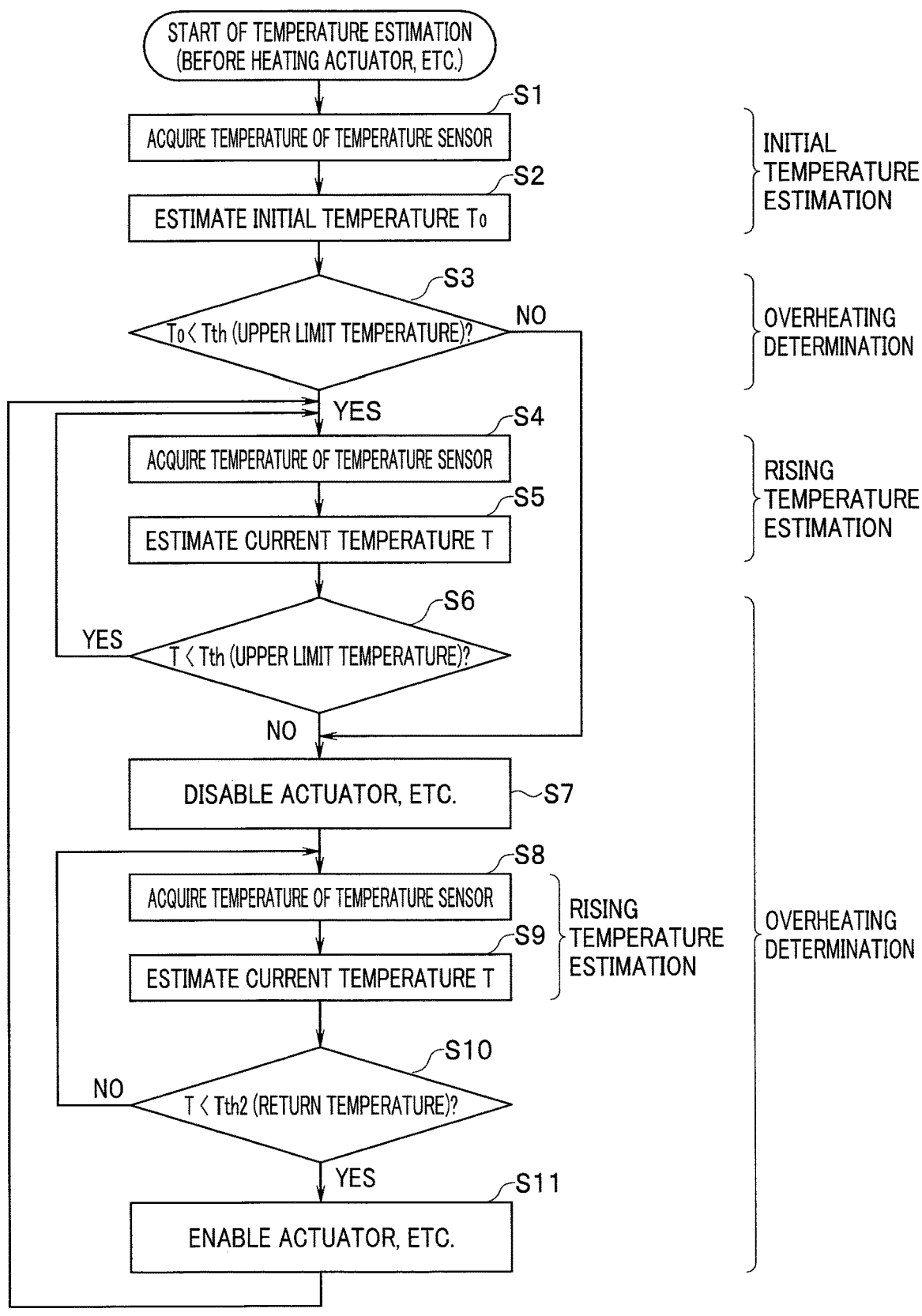

START OF TEMPERATURE ESTIMATION
(BEFORE HEATING ACTUATOR, ETC.)

S1

ACQUIRE TEMPERATURE OF TEMPERATURE SENSOR

S2

ESTIMATE INITIAL TEMPERATURE $T_0$

} INITIAL TEMPERATURE ESTIMATION

S3

$T_0$ < $T_{th}$ (UPPER LIMIT TEMPERATURE)?     NO

} OVERHEATING DETERMINATION

YES

S4

ACQUIRE TEMPERATURE OF TEMPERATURE SENSOR

S5

ESTIMATE CURRENT TEMPERATURE $T$

} RISING TEMPERATURE ESTIMATION

S6

YES     $T$ < $T_{th}$ (UPPER LIMIT TEMPERATURE)?

NO

DISABLE ACTUATOR, ETC.     S7

S8

ACQUIRE TEMPERATURE OF TEMPERATURE SENSOR

S9

ESTIMATE CURRENT TEMPERATURE $T$

} RISING TEMPERATURE ESTIMATION

S10

NO     $T$ < $T_{th2}$ (RETURN TEMPERATURE)?

YES

S11

ENABLE ACTUATOR, ETC.

} OVERHEATING DETERMINATION $T_H$
$R_1$
HEATER

T
$R_2$
ENDOSCOPE SURFACE $T_e$
SURROUNDING ENVIRONMENT $T_H$
$R_1$
HEATER

T
$R_2$
ENDOSCOPE SURFACE $T_e$
SURROUNDING ENVIRONMENT

ENDOSCOPE SYSTEM, PROCESSOR, AND METHOD FOR ESTIMATING TEMPERATURE OF ENDOSCOPE

CROSS REFERENCE TO RELATED APPLICATION

This application is a continuation application of PCT/JP2021/010709 filed on Mar. 16, 2021, the entire contents of which are incorporated herein by this reference.

BACKGROUND OF THE INVENTION

1. Field of the Invention

The present invention relates to an endoscope system that includes a processor configured to change rigidity of an insertion portion, a processor configured to change rigidity of an insertion portion, as well as to a method for estimating temperature of an endoscope.

2. Description of the Related Art

Conventionally, various systems have been known as variable-rigidity apparatuses serving as an actuator configured to change rigidity of an insertion portion. As a system of the variable-rigidity apparatus, a system that increases rigidity by heating a shape-memory alloy (SMA) member with a heater coil is known. For example, International Publication No. 2018/189888 discloses a configuration in which a shape-memory alloy (SMA) member is formed into a pipe shape and a heating element (heater coil) is placed coaxially with the SMA pipe.

The insertion portion tends to undergo increases in surface temperature due to heat generation and the like caused by an illumination optical system installed inside as well as by an actuator using a heater coil, such as described above. Therefore, a method for detecting the surface temperature of the insertion portion and keeping the surface temperature of the insertion portion from increasing is being studied.

Techniques for estimating the surface temperature of the insertion portion and keeping the surface temperature to or below appropriate temperature are known (Japanese Patent Application Laid-Open Publication No. 2020-116147, Japanese Patent Application Laid-Open Publication No. 2010-187903, Japanese Patent No. 5535305).

A method for estimating absolute temperature on a surface of a distal end portion of an endoscope using a single temperature sensor placed at a distance from the surface and a simple thermal network model has been proposed (Japanese Patent No. 5411086).

Here, in a process of inserting an endoscope into a subject, an endoscopic surgeon may pull the endoscope out of a processor and then plug the endoscope into the processor again, or power off the processor once and then power on the processor again. If such an action is carried out during the use of an actuator or the like, which is a heat source, it is assumed that initial surface temperature of the insertion portion is higher when the use of the insertion portion is resumed. In other words, the initial temperature of a surface of the insertion portion will vary in a wide range from minimum temperature (e.g., 10° C.) of an examination room to overheating detection temperature (e.g., 48° C.) of the surface of the insertion portion.

SUMMARY OF THE INVENTION

An endoscope system according to one aspect of the present invention includes: an endoscope equipped with an insertion portion inserted into a subject; a heating element provided in the insertion portion and configured to generate heat; a temperature sensor configured to acquire heating element temperature data on temperature of the heating element; and a processor. The processor outputs initial surface temperature, which is data on insertion portion surface temperature at a first time point prior to a heating start time of the heating element, based on the heating element temperature data at the first time point and estimates changes in the insertion portion surface temperature over time after the first time point based on the heating element temperature data after the first time point using the initial surface temperature as an initial value of the insertion portion surface temperature.

A processor according to one aspect of the present invention: acquires heating element temperature data from a temperature sensor configured to estimate temperature of a heating element provided in an insertion portion of an endoscope inserted into a subject; outputs initial surface temperature, which is insertion portion surface temperature at a first time point prior to a start of heating of the heating element, based on the heating element temperature data at the first time point, and estimates changes in the insertion portion surface temperature over time after the first time point based on the heating element temperature data after the first time point using the initial surface temperature as an initial value of the insertion portion surface temperature.

A method for estimating temperature of an endoscope according to one aspect of the present invention is a temperature estimation method for an endoscope that includes an insertion portion inserted into a subject, a heating element provided in the insertion portion and configured to generate heat, and a temperature sensor configured to measure temperature of the heating element, the method including: outputting initial surface temperature, which is insertion portion surface temperature at a first time point prior to a start of heating of the heating element, based on the heating element temperature data at the first time point; and estimating changes in the insertion portion surface temperature over time after the first time point based on the heating element temperature data after the first time point using the initial surface temperature as an initial value of the insertion portion surface temperature.

BRIEF DESCRIPTION OF THE DRAWINGS

FIG. 3 is a flowchart showing an endoscope surface temperature estimation operation performed by a rising temperature estimation unit of the endoscope system according to the first embodiment;

DETAILED DESCRIPTION OF THE PREFERRED EMBODIMENTS

Embodiments of the present invention will be described below using the drawings.

First Embodiment

Figure 1:
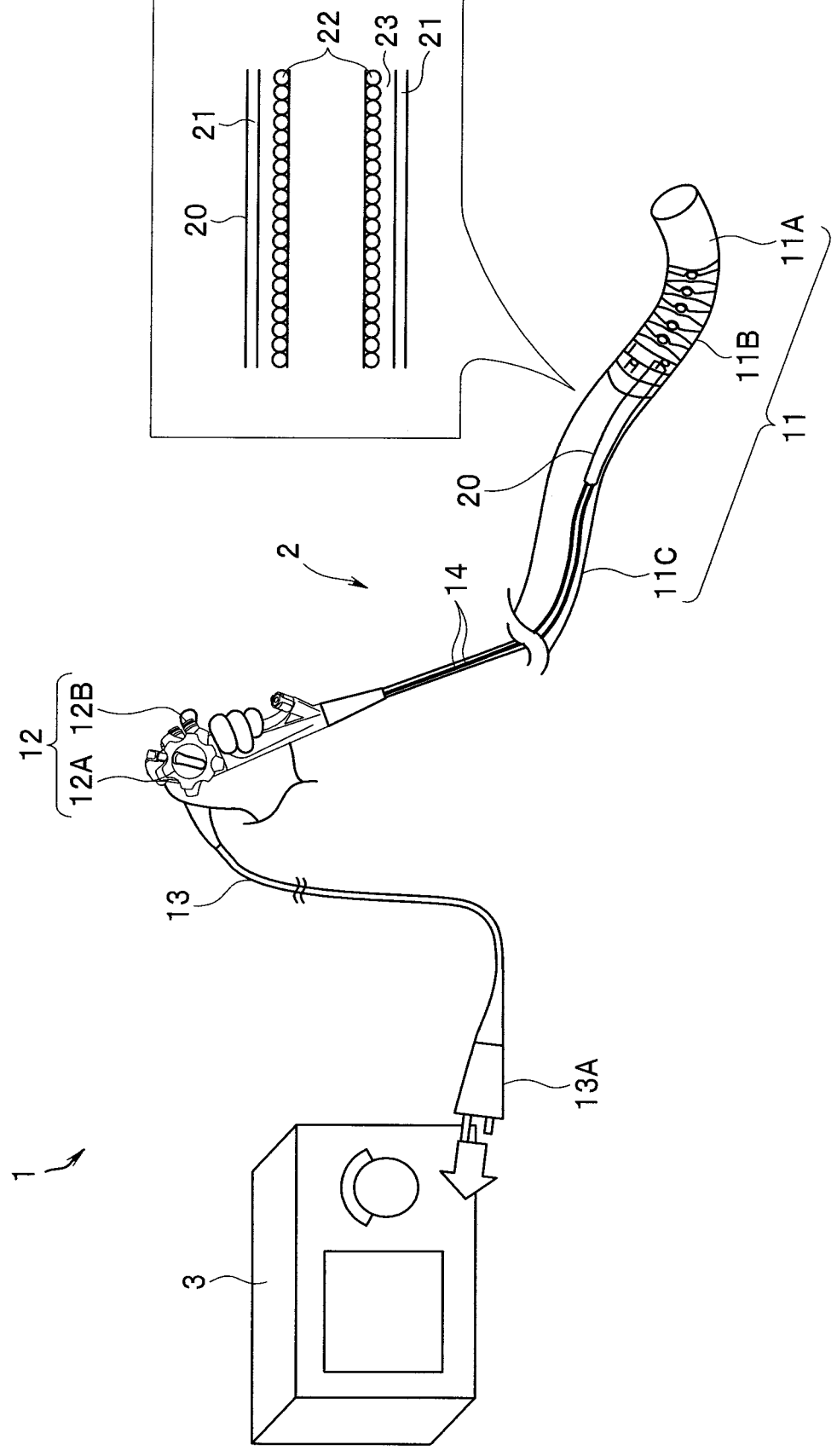
FIG. 1 is an external perspective view of principal part showing a configuration of an endoscope system according to a first embodiment of the present invention.
Figure 2:
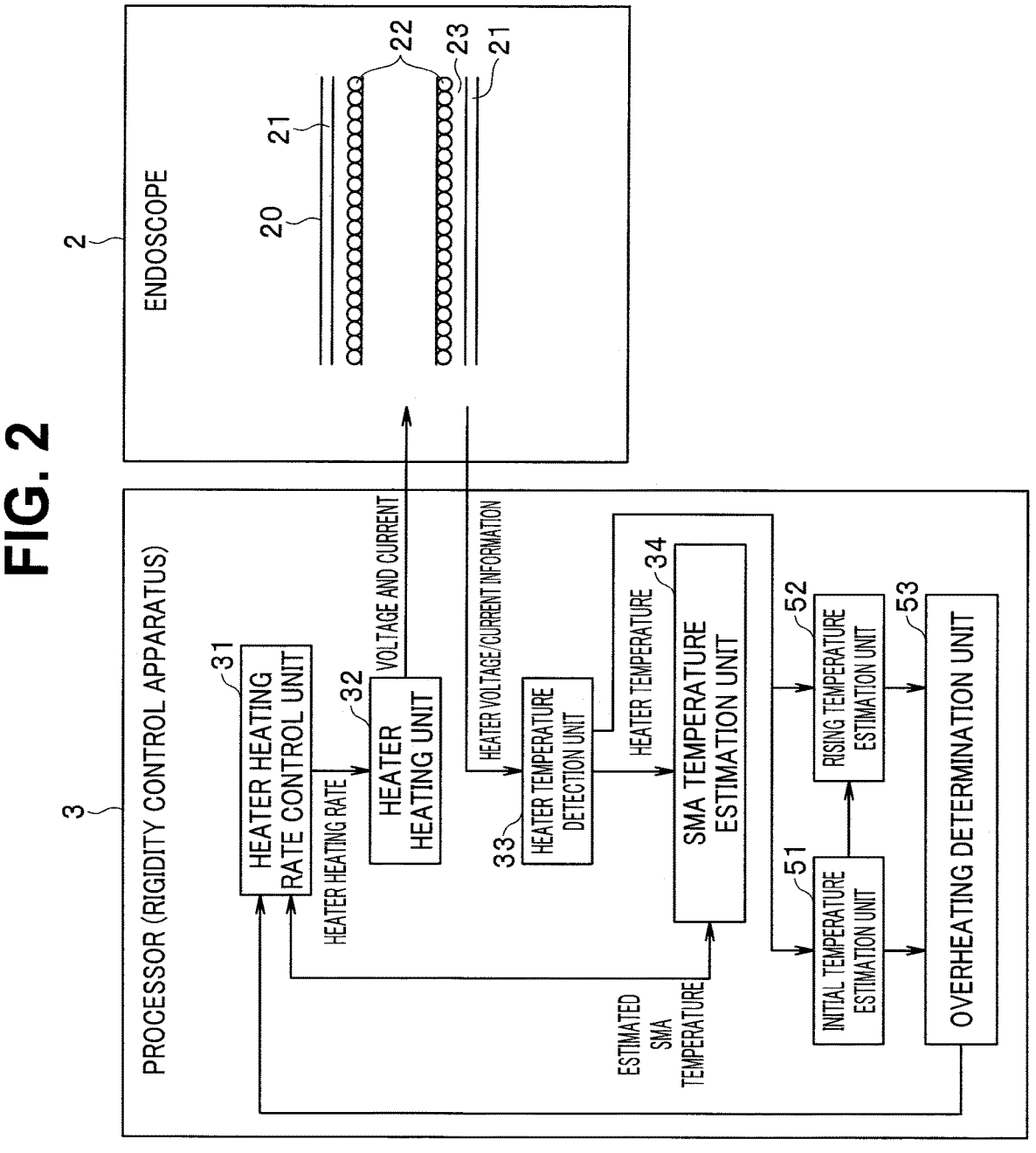
FIG. 2 is a block diagram showing major components of an endoscope and a processor making up the endoscope system according to the first embodiment.

FIG. 1 is an external perspective view of principal part showing a configuration of an endoscope system according to a first embodiment of the present invention, and FIG. 2 is a block diagram showing major components of an endoscope and a processor making up the endoscope system according to the first embodiment.

As shown in FIGS. 1 and 2, an endoscope system 1 according to the first embodiment of the present invention mainly includes an endoscope 2 inserted into a subject and used to pick up endoscopic images in a body cavity, and a processor 3 connected to the endoscope 2 and configured to apply predetermined image processing to acquired endoscopic images and output the resulting endoscopic images to the outside.

The endoscope 2 includes an insertion portion 11 inserted into the subject, an operation portion 12 provided on a proximal end side of the insertion portion 11, and a universal cord 13 extended form the operation portion 12. The endoscope 2 is configured to be detachably connected to the processor 3 via a scope connector 13A provided in an end portion of the universal cord 13.

In the present embodiment, the processor 3 contains a non-illustrated light source device. A light guide (not shown) for use to transmit illuminating light supplied from the light source device as well as a predetermined electric cable 14 extended from the processor 3 are disposed inside the insertion portion 11, the operation portion 12, and the universal cord 13.

The insertion portion 11 has flexibility and an elongated shape. Starting from a distal end side, the insertion portion 11 includes a rigid, distal end portion 11A, a bending portion 11B configured to be bendable, and a long, flexible tubular portion 11C having flexibility.

The distal end portion 11A is provided with an illuminating window (not shown) for use to emit illuminating light to the subject, where the illuminating light is transmitted through the light guide provided inside the insertion portion 11. The distal end portion 11A is provided also with an image pickup unit (not shown) configured to operate in response to an image pickup control signal supplied from the processor 3 and pick up an image of the subject illuminated by the illuminating light emitted through the illuminating window and output an image pickup signal. The image pickup unit includes an image sensor such as a CMOS image sensor or CCD image sensor.

The bending portion 11B is configured to be bendable in response to operation of an angle knob 12A provided on the operation portion 12.

According to the present embodiment, although details will be described later, in a variable-rigidity range, which corresponds to a predetermined range from a proximal end portion of the bending portion 11B to a distal end portion of the flexible tubular portion 11C, a variable-rigidity member (actuator) 20 is provided in a longitudinal direction of the insertion portion 11, being configured to be able to change flexural rigidity of the variable-rigidity range under the control of the processor 3 (rigidity control apparatus).

In the present embodiment, the variable-rigidity member 20 is an actuator configured to change bending of the insertion portion 11 and includes a heater 22, and thus can be seen as a heating element in the endoscope. In the present embodiment, as described in detail later, the variable-rigidity member 20 detects temperature of the heater 22 based on values of voltage and current supplied by the processor 3 to the heater 22, and thus the variable-rigidity member 20 (heater 22) also serves a function of a temperature sensor. Note that a concrete configuration and the like of the variable-rigidity member 20 will be described in detail later.

The operation portion 12 is shaped to be gripped and operated by a user. The operation portion 12 is provided with the angle knob 12A configured to be operated to allow the bending portion 11B to be bent in four—upward, downward, left, right (UDLR)—directions intersecting a longitudinal axis of the insertion portion 11. The operation portion 12 is provided with one or more scope switches 12B capable of giving instructions according to user input operation.

<Variable-Rigidity Member (Actuator, Heating Element, Temperature Sensor) 20>

As shown in FIGS. 1 and 2, the variable-rigidity member 20 serving also as an actuator, a heating element, and a temperature sensor is made up of an SMA pipe 21, a heater 22, and a thermally conductive member 23 and configured to be able to change flexural rigidity of the variable-rigidity range under the control of the processor 3.

The SMA pipe 21, which is formed of a shape-memory alloy (SMA) member exhibiting a small-diameter pipe shape, is a variable-rigidity member that increases in flexural rigidity when heated. The SMA pipe 21 according to the present embodiment is disposed in the longitudinal direction of the insertion portion 11 in a predetermined range from the proximal end portion of the bending portion 11B to the distal end portion of the flexible tubular portion 11C in the insertion portion 11 of the endoscope 2.

The heater 22 is made up of a heater coil disposed in a longitudinal direction in an inner diameter portion of the SMA pipe 21. The heater coil is formed by winding an electric conductor (heating wire) coaxially with an axis of the SMA pipe 21 into a substantially cylindrical shape, where the electric conductor, which has electrical conductivity, generates heat by being supplied with electric power.

In the present embodiment, the heater 22 is placed on an inner side of the SMA pipe 21, which is the variable-rigidity member, and disposed in the longitudinal direction with an outer peripheral portion of the cylindrical coil substantially abutting the inner diameter portion of the SMA pipe 21.

Note that in the present embodiment, the heater 22 is connected to the heater heating unit 32 of the processor 3 and generates heat by being supplied with electric power from the heater heating unit 32. Heating control of the heater 22 is performed by a heater heating rate control unit 31 and an overheating determination unit 53 similarly disposed in the processor 3.

When the heater 22 generates heat by being supplied with electric power, a resistance value of the heater 22 changes with temperature changes, and a voltage value and a current value on a power supply line connected to the heater 22 change accordingly. In the present embodiment, when the voltage value and the current value on the power supply line is measured, data about the resistance value of the heater 22 is fed back to the processor 3, temperature of the heater 22 is detected from the data about the resistance value of the heater 22, and moreover, temperature of the SMA pipe 21 is estimated from the temperature of the heater 22. The detection of the heater temperature and the estimation of the temperature of the SMA pipe 21 will be described in detail later.

Note that a technique described in International Publication No. 2018/189888 may be used for the configurations of the SMA pipe 21 and the heater 22, but in the present embodiment, a space between the heater 22 and the SMA pipe 21 is filled with the thermally conductive member 23 not adopted by the technique described in International Publication No. 2018/189888.

As described above, the thermally conductive member 23 is a characteristic component adopted in the present embodiment and is made of thermally conductive material, thermal conductivity of which is at least higher than air. In the present embodiment, a clearance portion between the heater 22 and the inner diameter portion of the SMA pipe 21, which is the variable-rigidity member, is filled with the thermally conductive member 23, which serves a role of efficiently transmitting heat generated by the heater 22 to the SMA pipe 21.

In this way, by placing the thermally conductive member 23 between the SMA pipe 21, which is the shape-memory alloy (SMA) member, and the heater 22, which is the heater coil, the present embodiment achieves the effect of reducing a temperature difference between the shape-memory alloy member and the heater coil.

<Configuration of Processor 3>

In the present embodiment, the processor 3 has various publicly known functions of a so-called video processor (image processing apparatus), such as a function of applying predetermined image processing to endoscopic images acquired through connection to the endoscope 2 and outputting the resulting endoscopic images to the outside and a function of controlling the connected endoscope 2, but detailed description of the publicly known functions of the image processing apparatus will be omitted, and components having functions characteristic of the present embodiment will be described below.

FIG. 2 is a block diagram showing major components of the endoscope and the processor making up the endoscope system according to the first embodiment.

As shown in FIG. 2, the processor 3 according to the present embodiment includes functions of the rigidity control apparatus configured to estimate and control the rigidity of the variable-rigidity member 20 by detecting the temperature of the heater 22 in the variable-rigidity member 20 of the endoscope 2 and a function to estimate surface temperature of the insertion portion 11 of the endoscope 2 in addition to including components related to non-illustrated publicly known image processing functions.

<Heater Temperature Detection and Rigidity Control of Variable-Rigidity Member>

Specifically, the processor 3 includes the heater beating unit 32 connected to the variable-rigidity member 20, which is a heating element, the heater heating rate control unit 31 configured to control the heater heating unit 32, a heater temperature detection unit 33 configured to detect the temperature of the heater 22 in the variable-rigidity member 20, and an SMA temperature estimation unit 34 configured to estimate the temperature of the SMA pipe 21 based on the temperature of the heater 22 detected by the heater temperature detection unit 33.

Note that at least any of the multiple components of the processor 3 may be made up of an internal circuit of a software-based processor or may be made up of a dedicated hardware circuit. For example, the heater heating rate control unit 31 may be made up of an internal circuit of a software-based processor or may be made up of a dedicated hardware circuit (control circuit).

A program configured to implement a processor on a computer may be stored in a non-transitory computer-readable storage medium.

When the endoscope 2 is connected to the processor 3, the heater heating unit 32 supplies electric power to the heater 22 in the variable-rigidity member 20 disposed in the endoscope 2 through the power supply line to cause the heater 22 to generate heat. In so doing, the heater heating unit 32 supplies the electric power under the control of the heater heating rate control unit 31 (or under the control of the overheating determination unit 53 in some cases) based on heater heating rate data acquired from the heater heating rate control unit 31.

The heater heating rate control unit 31 acquires predetermined target SMA temperature, calculates a heater heating rate to apply electric power to the heater 22 based on the acquired target SMA temperature and estimated SMA temperature acquired from the SMA temperature estimation unit 34, and transmits data on the heater heating rate to the heater heating unit 32.

Note that the heater heating rate control unit 31 also has a function to estimate rigidity of the SMA pipe 21 based on the estimated SMA temperature acquired from the SMA temperature estimation unit 34.

The heater temperature detection unit 33 acquires voltage/current data on the heater 22 from the endoscope 2. For example, the heater temperature detection unit 33 acquires data on heater voltage by being connected to a signal line used to measure voltage across the heater 22 and acquires heater current by being connected to a power supply line used to supply electric power intended to heat the heater 22. Then, the heater temperature detection unit 33 successively acquires data on the resistance value of the heater 22 based on the acquired voltage/current data on the heater 22. Furthermore, the heater temperature of the heater 22 is calculated successively from a relational expression between the heater resistance value and the heater temperature.

The SMA temperature estimation unit 34 acquires data on the heater temperature of the heater 22 calculated by the heater temperature detection unit 33 and estimates the temperature (SMA temperature) of the SMA pipe 21 (hereinafter abbreviated to SMA in some cases), which is a shape-memory member. In so doing, the SMA temperature estimation unit 34 estimates the SMA temperature of the SMA pipe 21 based on a "thermal conductivity model" that takes into consideration respective thermal conductivity properties of "a member between the heater 22 and the SMA pipe 21," "the SMA pipe 21 itself," and "a surrounding environment of the SMA pipe 21" in addition to the acquired heater temperature data.

<Insertion Portion Surface Temperature Estimation Function>

Furthermore, in the present embodiment, the processor 3 includes an initial temperature estimation unit (initial surface temperature estimation unit) 51 configured to estimate initial surface temperature out of the surface temperature of the insertion portion 11 based on the temperature data of the heater 22 calculated by the heater temperature detection unit 33, a rising temperature estimation unit 52 configured to estimate rising surface temperature of the insertion portion 11 also based on the temperature data of the heater 22 calculated by the heater temperature detection unit 33, after the heater 22 in the variable-rigidity member 20, which is a heating element, is heated, and the overheating determination unit 53 configured to determine overheating of the heater 22 also based on the temperature data of the heater 22 calculated by the heater temperature detection unit 33.

The endoscope system according to the present embodiment performs initial temperature estimation of an insertion portion surface and temperature estimation of the insertion portion surface after the initial temperature using different estimation equations. In other words, by estimating initial temperature of an endoscope surface in a limited situation (e.g., just before heating a heating element such as an actuator (the variable-rigidity member 20 in the present embodiment)) and estimating subsequent endoscope surface temperature using results of the initial temperature estimation, it is possible to maintain high estimation accuracy and high stability.

<Overview of Insertion Portion Initial Surface Temperature Estimation>

In the present embodiment, the initial temperature (absolute temperature of the endoscope surface just before heating the heating element such as the actuator (the variable-rigidity member 20 in the present embodiment)) of the insertion portion surface is estimated.

Note that according to the present embodiment, in the variable-rigidity member 20 disposed in the insertion portion 11, because the heater 22 installed inside corresponds to a heating element and the variable-rigidity member 20 itself serves a role of a temperature sensor (in the processor 3, because the temperature of the heater 22 is detected by measuring voltage and current values of the electric power supplied to the heater 22, it can be said that the variable-rigidity member 20 serves the role of a temperature sensor), the initial temperature is estimated using detection temperature of the heater 22 in the variable-rigidity member 20, which is also a temperature sensor, as an input and using a heat conduction model that takes into consideration thermal conductivity from the heater 22 in the variable-rigidity member 20 to the endoscope surface as well as heat transfer between the endoscope surface and the surrounding environment.

By performing the initial temperature estimation at a time point other than during heating and ignoring the impact of the initial temperature estimation by regarding that the rate of change in endoscope surface temperature is low, responsiveness of endoscope surface temperature estimation can be increased.

<Overview of Endoscope Surface Temperature Estimation after Initial Temperature>

After the initial temperature estimation, subsequent endoscope surface temperature is estimated using the initial temperature. Here, the endoscope surface temperature after the initial temperature is stably estimated with high accuracy using the detection temperature of the temperature sensor (in the present embodiment, the detection temperature of the heater 22 in the variable-rigidity member 20, which is also a temperature sensor, as described above) as an input and using a heat conduction model that takes into consideration heat capacity of the insertion portion, thermal conductivity between the heating element (heater 22) and the endoscope surface, and heat transfer between the endoscope surface and the surrounding environment.

<Temperature Estimation Operation of Insertion Portion Surface Temperature According to First Embodiment>

Next, a temperature estimation operation of insertion portion surface temperature according to the first embodiment will be described with reference to a flowchart shown FIG. 3.

FIG. 3 is a flowchart showing an endoscope surface temperature estimation operation performed by the rising temperature estimation unit of the endoscope system according to the first embodiment.

As shown in FIG. 3, just before the heater 22 in the variable-rigidity member 20, which is a heating element, is heated, the initial temperature estimation unit 51 starts estimating the surface temperature (initial surface temperature estimation) of the insertion portion 11. First, the initial temperature estimation unit 51 acquires temperature data (heating element temperature data) at a first time point prior to a heating start time of the heater 22 serving the role of a temperature sensor from the heater temperature detection unit 33 (step S1) and estimates initial surface temperature $T_0$ of the insertion portion 11 (step S2). Note that a technique for estimating the initial surface temperature $T_0$ based on the heating element temperature data only at the first time point will be described in detail later.

Next, the overheating determination unit 53 determines whether the initial surface temperature $T_0$ of the insertion portion 11 is lower than a predetermined upper limit value $T_{th}$ (step S3). If it is determined in step S3 that the initial surface temperature $T_0$ of the insertion portion 11 is lower than the predetermined upper limit value $T_{th}$, the heater 22 in the variable-rigidity member 20, which is a heating element, starts heating. In other words, the heater 22 in the variable-rigidity member 20 is heated by being supplied with electric power from the heater heating unit 32 under the control of the heater heating rate control unit 31, and accordingly the surface temperature of the insertion portion 11 starts to increase gradually.

When the heater 22 starts heating, the rising temperature estimation unit 52 sets the initial surface temperature $T_0$ as an initial value of the surface temperature of the insertion portion, then acquires temperature data of the heater 22 after the first time point from the heater temperature detection unit 33 (step S4), and estimates rising surface temperature T of the insertion portion 11 based on the acquired temperature data of the heater 22 (step S5). In other words, the rising temperature estimation unit estimates changes in the insertion portion surface temperature over time after the first time point based on the heating element temperature data after the first time point. Note that a technique for estimating the rising surface temperature T will be described in detail later.

On the other hand, the overheating determination unit 53 continues to monitor whether the rising surface temperature T of the insertion portion 11 reaches the predetermined upper limit value $T_{th}$ (step S6), and the rising temperature estimation unit 52 repeats steps S4 and S5 until the rising surface temperature T of the insertion portion 11 reaches the predetermined upper limit value $T_{th}$.

In step S6 described above, if the rising surface temperature T of the insertion portion 11 reaches the predetermined upper limit value $T_{th}$, i.e., if it is determined that the surface temperature of the insertion portion 11 corresponds to overheating, the actuator function of the variable-rigidity member 20 is stopped once (step S7). In so doing, in the present embodiment, under the control of the heater heating rate control unit 31, heating of the heater 22 in the variable-rigidity member 20 is stopped to allow heat to dissipate spontaneously.

Subsequently, along with the stop of the heating of the heater 22, the rising temperature estimation unit 52 acquires the temperature data of the heater 22 from the heater temperature detection unit 33 (step S8), and estimates the current value of the rising surface temperature T of the insertion portion 11 based on the acquired temperature data of the heater 22 (step S9).

At the same time, the overheating determination unit 53 continues to monitor the rising surface temperature T of the insertion portion 11, and when the rising surface temperature T falls below predetermined return temperature $T_{th2}$ (step S10), the heater heating rate control unit 31 enables heating of the heater 22 in the variable-rigidity member 20 and enables the actuator function of the variable-rigidity member 20 (step S11).

<Operation of Rising Temperature Estimation Unit 52>

Next, detailed description will be given of the operation of estimating the rising surface temperature of the insertion portion 11 performed by the rising temperature estimation unit 52 according to the present embodiment.

The rising temperature estimation unit 52 creates a heat conduction model from the heat conduction equation shown below, and estimates the endoscope surface temperature of the insertion portion 11 using the Laplace transform of the heat conduction model as a linear transfer function, the heater temperature as input, and estimated endoscope surface temperature as output.

Note that in the temperature estimation performed by the rising temperature estimation unit 52, "gain," "time constant," and "surrounding environment temperature" are all fixed values.

[Heat Conduction Equation According to First Embodiment]

$$mc\frac{dT}{dt} = \frac{kA}{D}(T_H - T) - hA_s(T - T_e) - \varepsilon\sigma A_s(T^4 - T_e^4)$$

$T_H$: Heater temperature [K] (input value),
T: Endoscope surface temperature [K] (output value),
$T_e$: Surrounding environment temperature [K],
m: Mass of endoscope surface [g],
c: Specific heat of endoscope surface [J/g/K],
k: Average thermal conductivity of endoscope.
D: Average thickness from heater coil to endoscope surface,
A: Average cross-sectional area from heater coil to endoscope surface, h: Average thermal conductivity.
$A_S$: Virtual surface area of endoscope [m²],
ε: Emissivity,
σ: Stefan-Boltzmann coefficient

[Heat Conduction Model Used by Rising Temperature Estimation Unit 52 According to First Embodiment]

$$C\frac{d(T - T_e)}{dt} = \frac{1}{R_1}(T_H - T) - \frac{1}{R_2}(T - T_e)$$

Figure 4:
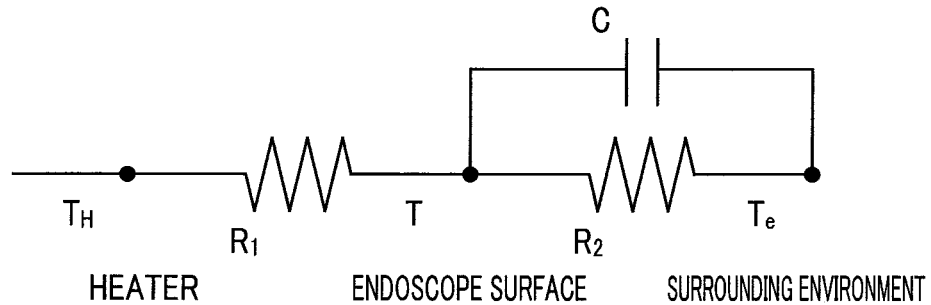
FIG. 4 is an equivalent circuit diagram showing an example of a heat conduction model used by the rising temperature estimation unit of the endoscope system according to the first embodiment.

An example of constant parameters of a heat conduction model used by the rising temperature estimation unit 52 is shown in FIG. 4.

$T_H$: Heater temperature [K] (input value).
T: Endoscope surface temperature [K] (output value),
$T_e$: Surrounding environment temperature [K]
C: Heat capacity from endoscope surface to surrounding environment,
R1: Thermal resistance from heater coil to endoscope surface,
R2: Thermal resistance from endoscope surface to surrounding environment

[Linear Transfer Function Resulting from Laplace Transform of Heat Conduction Model]

The linear transfer function resulting from the Laplace transform of the heat conduction model is as follows.

$$T - T_e = \frac{K}{1 + \tau s}(T_H - T_e)$$

$$\text{Gain } K = \frac{1}{1 + \frac{R_1}{R_2}}$$

$$\text{Time constant } \tau = \frac{C}{\frac{1}{R_1} + \frac{1}{R_2}}$$

where "S" is a Laplace operator, which has a meaning of a time derivative, and the endoscope surface temperature T, which is an output value, rises temporally smoothly.

[Concrete Example of Implementation Method]

Regarding methods for discretizing (z transformation) a transfer function in an s region such as described above, bilinear transformation, backward difference approximation, and the like are generally known. In the present embodiment, an implementation method that uses bilinear transformation will be shown below.

$$T(s) - T_e = \frac{K}{1 + \tau s}(T_H(s) - T_e)$$

is bilinearly transformed into $$T[t] = a(T_H[t] - T_e) + a(T_H[t-1] - T_e) + b(T[t-1] - T_e) + T_e$$

$$a = \frac{K \cdot T_s}{T_s + 2\tau}$$

$$b = \frac{-T_s + 2\tau}{T_s + 2\tau}$$

$T_s$: Sampling period

<Operation of Initial Temperature Estimation Unit 51>

Next, detailed description will be given of the operation of estimating the initial surface temperature of the insertion portion 11 performed by the initial temperature estimation unit 51 according to the present embodiment.

The initial temperature estimation unit 51 estimates the initial surface temperature of the insertion portion 11 just before heating the heating element such as the actuator (the heater 22 in the variable-rigidity member 20 in the present embodiment). In so doing, because d(T−Te)/dt is not larger than during heating, responsiveness of estimation is increased by setting d(T−Te)/dt in the equation used by the rising temperature estimation unit 52 approximately equal to zero and the endoscope surface temperature of the insertion portion 11 is estimated instantaneously.

In other words, the initial temperature estimation unit 51 creates a heat conduction model from the heat conduction equation described above, finds a linear transfer function from the Laplace transform of the heat conduction model, and estimates the endoscope surface temperature using initial heater temperature as input, and estimated initial endoscope surface temperature as output.

Note that in the initial temperature estimation performed by the initial temperature estimation unit 51, "gain" and "surrounding environment temperature" are fixed values.

[Heat Conduction Model Used by Initial Temperature Estimation Unit 51 According to First Embodiment]

$$0 = \frac{1}{R_1}(T_{Ho} - T_o) - \frac{1}{R_2}(T_o - T_e)$$

Figure 5:
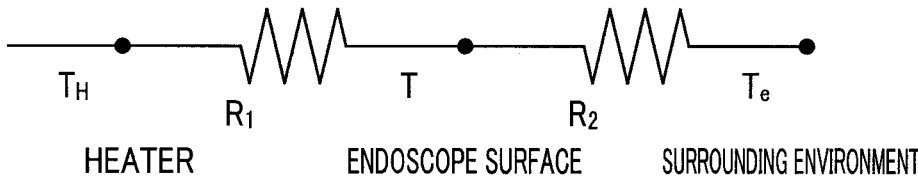
FIG. 5 is an equivalent circuit diagram showing an example of a heat conduction model used by an initial surface temperature estimation unit of the endoscope system according to the first embodiment.

An example of constant parameters of a heat conduction model used by the initial temperature estimation unit 51 is shown in FIG. 5.

$T_{HO}$: Initial heater temperature [K] (input value), $T_0$: Initial endoscope surface temperature [K] (output value), $T_e$: Surrounding environment temperature [K], R1: Thermal resistance from heater coil to endoscope surface, R2: Thermal resistance from endoscope surface to surrounding environment

[Linear Transfer Function Resulting from Laplace Transform of Heat Conduction Model]

The linear transfer function resulting from the Laplace transform of the heat conduction model is as follows.

$$T_0 - T_e = K(T_{HO} - T_e)$$

$$\text{Gain } K = \frac{1}{1 + \frac{R_1}{R_2}}$$

Figure 6:
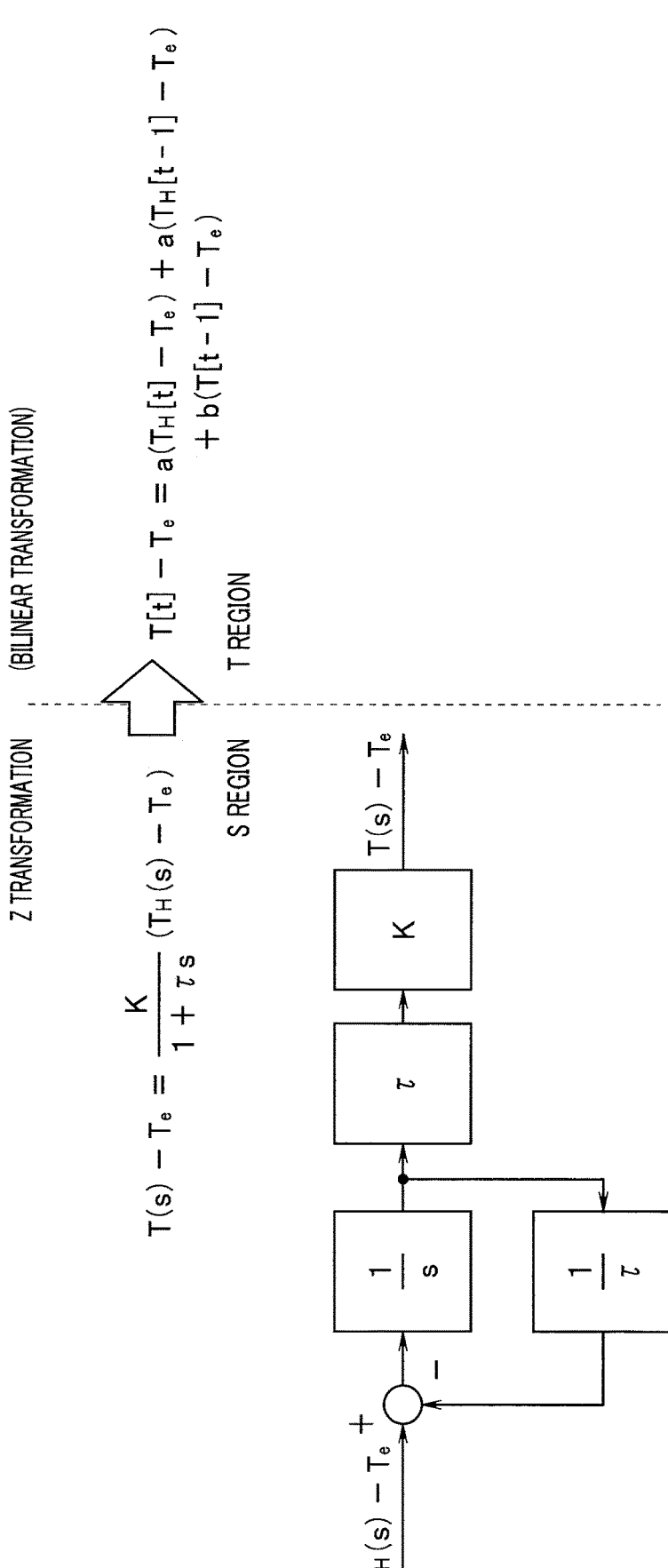
FIG. 6 is an explanatory diagram for illustrating equations used by the rising temperature estimation unit of the endoscope system according to the first embodiment.
Figure 7:
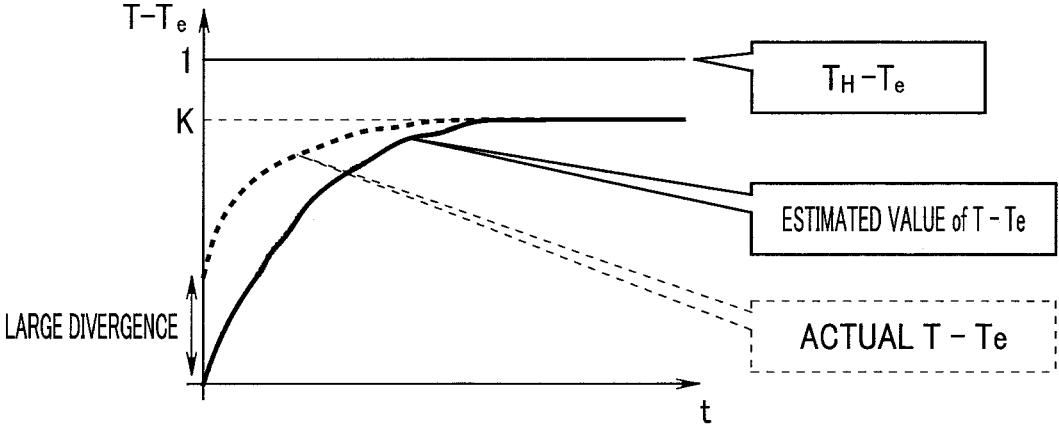
FIG. 7 is an explanatory diagram for illustrating estimated endoscope surface temperature characteristics in a case where the endoscope system according to the first embodiment does not include the initial surface temperature estimation unit.
Figure 8:
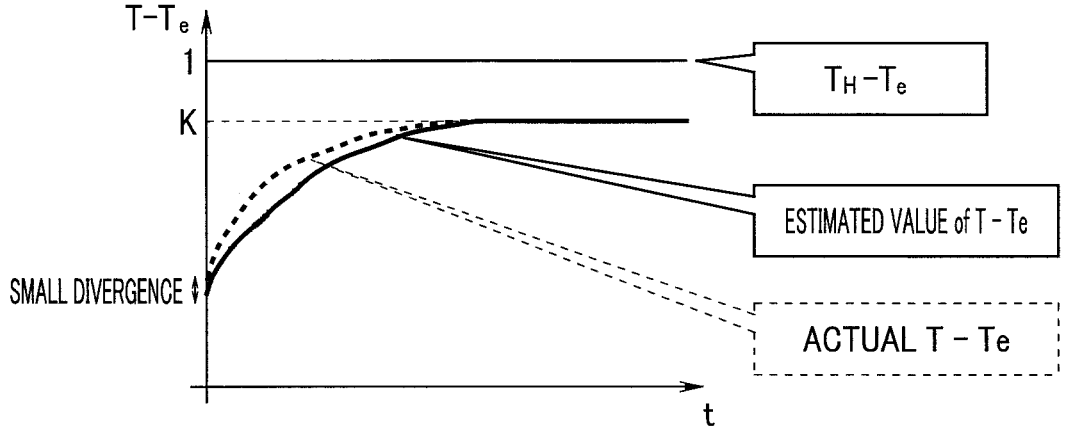
FIG. 8 is an explanatory diagram for illustrating estimated endoscope surface temperature characteristics in a case where the endoscope system according to the first embodiment includes the initial surface temperature estimation unit.

Next, the effect of estimating the initial temperature of the endoscope surface in the insertion portion 11, which is one of the features of the present embodiment, will be described with reference to FIG. 6 showing equations used by the rising temperature estimation unit, FIG. 7 showing a diagram of estimated endoscope surface temperature characteristics in a case where the initial surface temperature estimation unit does not exist, and FIG. 8 showing a diagram of estimated endoscope surface temperature characteristics in a case where the initial surface temperature estimation unit exists.

As shown in FIG. 6, as can also be seen from the transfer function in the s region and the equation of a t region obtained as a result of z transformation that involves bilinearly transforming the transfer function, the endoscope surface temperature "T" produced as output is affected by "T" at the previous time point.

Now, let us consider how the endoscope surface temperature T would be if the initial temperature estimation unit 51 did not exist and initial temperature of the insertion portion 11 were not estimated.

As an example in which the initial temperature of the insertion portion 11 is not estimated, a case in which the heater temperature $T_H$−the surrounding environment temperature $T_e$=1 will be considered, for the sake of simplicity.

When the initial temperature is not estimated, at t=0, (T[t−1]−Te) is hypothetically substituted with some constant (normally 0). Then, as can be seen from FIG. 7, if assumed initial temperature diverges greatly from the actual initial temperature (the endoscope surface temperature at t=0), temperature estimation accuracy remains low for some time. In other words, the estimated temperature diverges greatly from the actual temperature.

In contrast, when the initial temperature is estimated by installing the initial temperature estimation unit 51 as with the present embodiment, the divergence between the actual initial temperature (the endoscope surface temperature at t=0) and the estimated initial temperature is reduced as shown in FIG. 8, achieving the effect of maintaining a high degree of temperature estimation accuracy.

According to the present embodiment, the rising temperature estimation unit 52 and the initial temperature estimation unit 51 use different equations. The reason for this is as follows.

The rising temperature estimation unit 52 according to the present embodiment is a model that properly reflects actual phenomena, and thus basically has a high estimation accuracy. Moreover, the rising temperature estimation unit 52 is stable because velocity and the like are not used for input. However, because of a large time constant, if the estimated initial temperature diverges greatly from the actual temperature, it takes time for the estimated temperature to converge to the correct temperature (temperature close to the actual temperature). Actually, if the heater temperature changes abruptly, it takes time before the heat is conducted to the endoscope surface, causing the endoscope surface temperature to change. The time constant depends on a distance between the temperature sensor and the endoscope surface or on thermal conductivity and the like between the temperature sensor and the endoscope surface. If the temperature sensor can be placed very close to the endoscope surface, the time constant can be reduced, but it is often the case that this cannot be realized due to limitations of space and the like in the endoscope.

On the other hand, the initial temperature estimation unit 51 according to the present embodiment uses a model obtained by taking an impact of the rate of change in the endoscope surface temperature away from the model used by the rising temperature estimation unit 52. Since the time constant is close to 0, temperature close to the actual temperature can be estimated promptly. Then, by estimating the initial temperature in a situation in which the rate of change in the endoscope surface temperature is not high, temperature close to the actual temperature can be estimated promptly.

In this way, the two models for the rising temperature estimation unit 52 and the initial temperature estimation unit 51 adopted in the present embodiment have the respective features described above, and by using the estimation models according to situations, the present invention achieves the effect of being able to keep a high estimation accuracy.

Effect of First Embodiment

As described above, by estimating the absolute temperature of the insertion portion surface stably with high accuracy in every situation such as when the endoscope is pulled out of the processor and then plugged into the processor again during use of the endoscope, when the processor is restarted, or when the temperature of the heating element installed inside the insertion portion 11 fluctuates wildly with time, the endoscope system according to the first embodiment can perform control in order not to limit the use of the actuator and the like excessively while preventing the insertion portion surface from becoming hot.

Modification of First Embodiment

Next, a modification of the first embodiment will be described.

Whereas in the first embodiment, an example in which the variable-rigidity member 20 that functions as an actuator and a heating element also functions as a temperature sensor has been cited, an endoscope system according to the present modification is characterized in that the endoscope 2 includes not only the variable-rigidity member 20 functioning as an actuator and a heating element, but also a temperature sensor configured to detect the temperature of the variable-rigidity member 20, which is a heat source.

Figure 9:
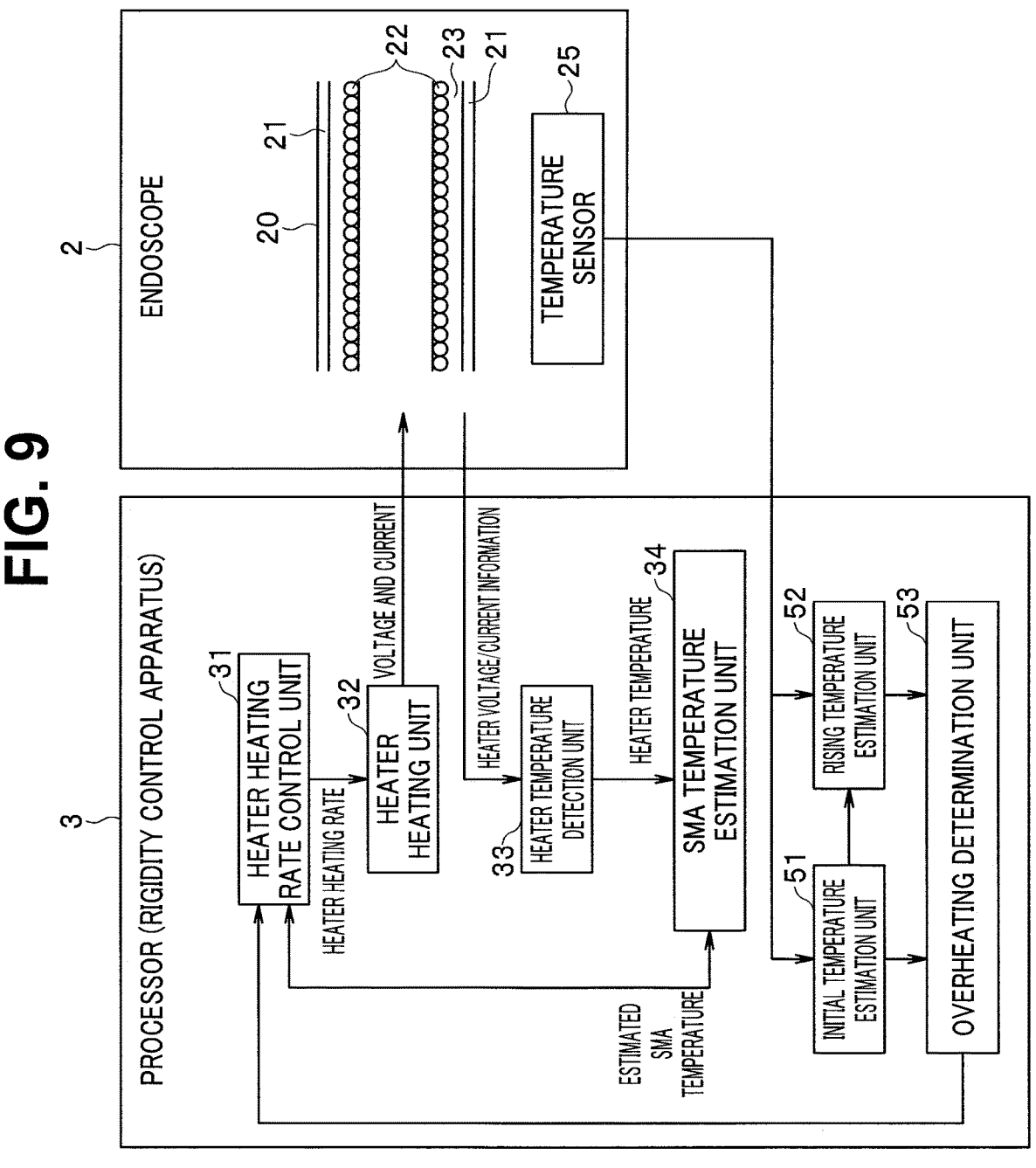
FIG. 9 is a block diagram showing major components of an endoscope and a processor making up an endoscope system according to a modification of the first embodiment.

FIG. 9 is a block diagram showing major components of an endoscope and a processor making up an endoscope system according to the modification of the first embodiment.

As shown in FIG. 9, a temperature sensor 25 configured to acquire heating element temperature data on the temperature of the heater 22 is disposed in the endoscope 2, where the heater 22 is a heating element included in the variable-rigidity member 20.

In the present modification, the initial temperature estimation unit 51 acquires temperature data from the temperature sensor 25 and estimates the initial surface temperature of the insertion portion 11 based on the temperature data just before the heating start time of the heater 22, which is a heating element. On the other hand, in the present modification, using the initial surface temperature estimated by the initial temperature estimation unit 51 as an initial value, the rising temperature estimation unit 52 estimates rising temperature of the insertion portion 11 based on the temperature data from the temperature sensor 25 after heating of the heater 22.

Note that other components, operations, and effects of the present modification are similar to the first embodiment, and thus description of components, operations, and effects similar to the first embodiment will be omitted and only differences will be described here.

Whereas in the first embodiment described above, the heater 22 included in the variable-rigidity member 20 has been cited as an example of the heating element, this is not restrictive, and when an image pickup device or a light-emitting element such as an LED disposed in a distal end portion of the insertion portion 11 can be assumed to be a heating element that affects surface temperature of the endoscope 2, the technical idea of the present invention described above is also applicable to such a device.

Second Embodiment

Next, a second embodiment of the present invention will be described.

An endoscope system according to the second embodiment is similar to the first embodiment in a basic configuration, and thus only differences will be described here.

The endoscope system according to the second embodiment is characterized in that out of consideration for safety, the initial temperature estimation unit 51 estimates the initial temperature at a little higher level in advance to absorb variations.

[Linear Transfer Function Resulting from Laplace Transform of Heat Conduction Model According to Second Embodiment]

According to the second embodiment, the linear transfer function resulting from the Laplace transform of the heat conduction model is as follows.

$$T_0 = K(T_{HO} - T_e) + T_e + \alpha$$

$\alpha$: Margin temperature $$\alpha = K_M(T_{HO} - T_e)$$

$K_M$: Fixed value. Different values may be set according to whether $T_{HO} > T_e$ or $T_{HO} < T_e$.

$K_M$ is set based on an actual measured value taken when the rate of change in the endoscope surface temperature is maximized (e.g., when heat is caused to dissipate spontaneously from an upper limit value of the endoscope surface temperature or when the endoscope is inserted into a body at temperature of approximately 40° C. from a minimum temperature environment of an examination room) in a situation in which the heating element such as the actuator is not heating.

Effect of Second Embodiment

In this way, the endoscope system according to the second embodiment is characterized in that the margin temperature (predetermined safety value) is added to the estimated initial temperature. Thus, even if there is a slight rate of change in the endoscope surface temperature during initial temperature estimation, by estimating temperature at a little higher level, variations can be absorbed, thereby achieving the effect of ensuring safety.

Third Embodiment

Next, a third embodiment of the present invention will be described.

An endoscope system according to the third embodiment is similar to the first embodiment in a basic configuration, and thus only differences will be described here.

An endoscope system according to the third embodiment is characterized in that the rising temperature estimation unit 52 uses both the power consumption of the heater 22 and the temperature of the heater 22 as input. In other words, if a difference in the estimated value of the endoscope surface temperature between when the heater temperature is used as input and when the heater power consumption is used as input is larger than a predetermined value, the rising temperature estimation unit 52 determines that the temperature sensor is faulty. In other words, in the third embodiment, the rising temperature estimation unit also serves as a failure detection unit. This makes it possible to determine failure of the temperature sensor precisely.

For example, when the temperature sensor is provided independently as with the modification of the first embodiment, if the temperature sensor itself fails, it is determined effectively that the temperature sensor has failed, and when the variable-rigidity member 20 itself functions as a temperature sensor as with the first embodiment, if temperature detection of the heater 22 by the heater temperature detection unit 33 of the processor 3 gets out of order, causing a divergence from the actual temperature, it can be determined precisely that acquisition of temperature data is out of order.

[Heat Conduction Model According to Third Embodiment]

$$C\frac{d(T - T_e)}{dt} = \dot{Q} - \frac{1}{R}(T - T_e)$$

$\dot{Q}$: Heater power consumption

Figure 10:
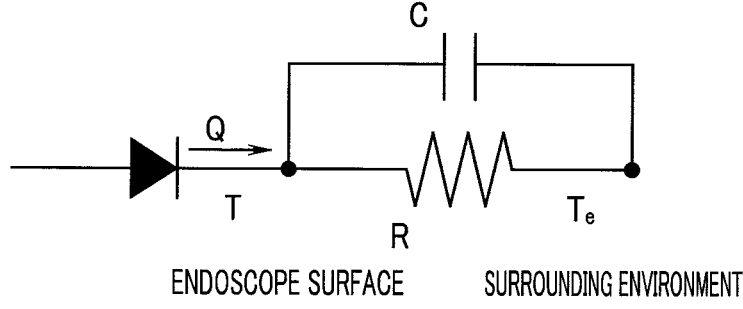
FIG. 10 is an equivalent circuit diagram showing an example of a heat conduction model used by a rising temperature estimation unit of an endoscope system according to a third embodiment of the present invention.

An example of constant parameters of a heat conduction model used by the rising temperature estimation unit 52 according to the third embodiment is shown in FIG. 10.

[Linear Transfer Function Resulting from Laplace Transform of Heat Conduction Model According to Third Embodiment]

$$T - T_e = \frac{K_Q}{1 + \tau_Q s}\dot{Q}$$

Gain $K_Q = R$

Time constant $\tau_Q = RC$

Effect of Third Embodiment

As described above, the third embodiment makes it possible to determine failure of the temperature sensor precisely.

Fourth Embodiment

Next, a fourth embodiment of the present invention will be described.

An endoscope system according to the fourth embodiment is similar to the first embodiment in a basic configuration, and thus only differences will be described here.

The fourth embodiment is characterized in that when the overheating determination unit 53 determines that the endoscope surface is overheated, the use of an actuator, which is a heating element having a temperature sensor function, is stopped, i.e., electric power supply to the temperature sensor, which itself generates heat, is stopped, and after an elapse of a predetermined period of time, the use of the actuator is permitted again and the process is resumed beginning with initial temperature estimation.

Figure 11:
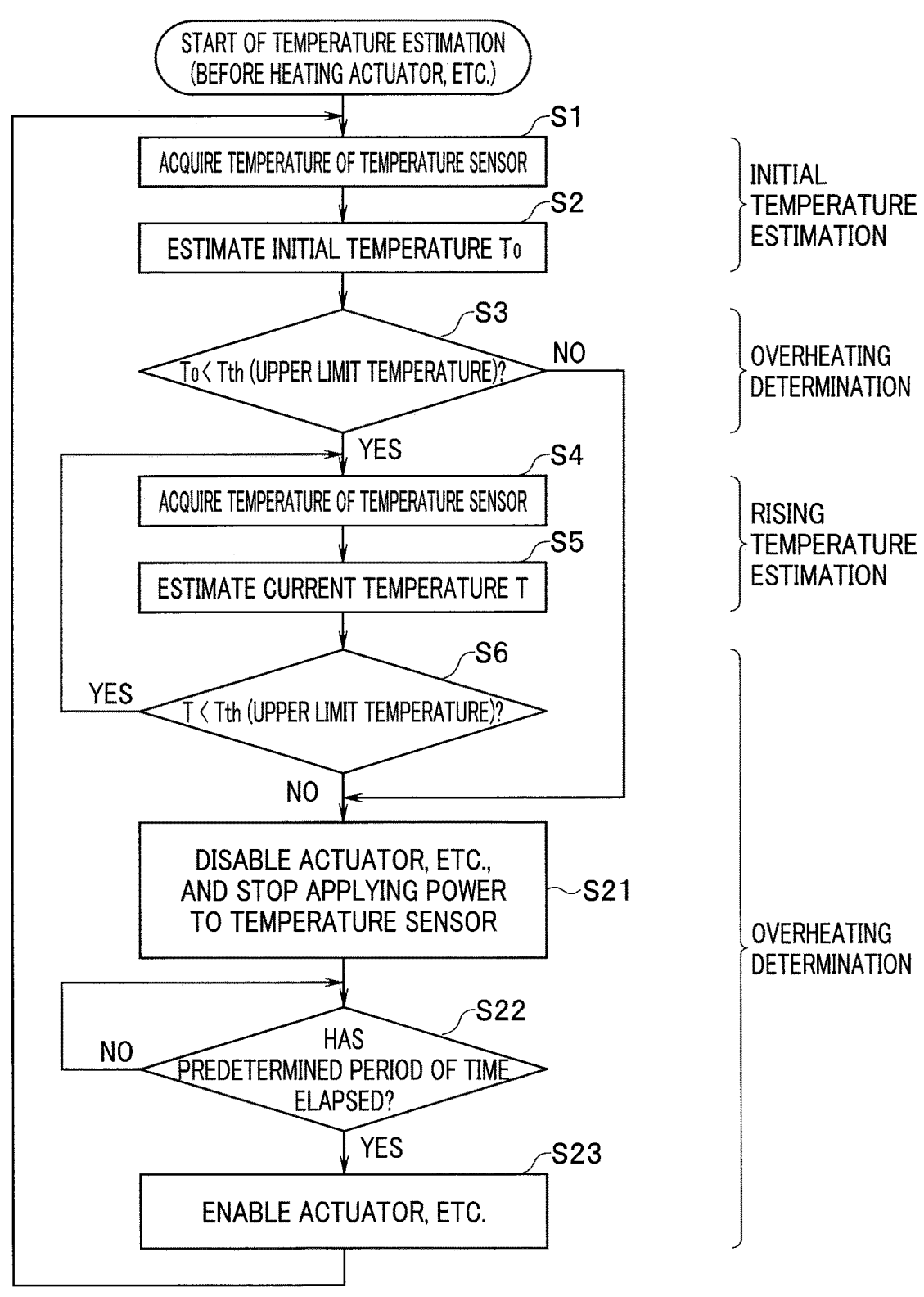
FIG. 11 is a flowchart showing an endoscope surface temperature estimation operation performed by a rising temperature estimation unit of an endoscope system according to a fourth embodiment of the present invention.

FIG. 11 is a flowchart showing an endoscope surface temperature estimation operation performed by the rising temperature estimation unit of the endoscope system according to the fourth embodiment of the present invention.

In FIG. 11, steps S1 to S6 are similar to the flowchart according to the first embodiment shown in FIG. 3, and thus description thereof will be omitted here.

In step S6, if the overheating determination unit 53 determines that the endoscope surface temperature T of the insertion portion 11 has exceeded the upper limit value $T_{th}$, the use of the variable-rigidity member 20 as an actuator is limited. i.e., electric power supply to the heater 22, which is a heating element having a temperature sensor function, is stopped (step S21). Subsequently, after an elapse of a certain period of time (step S22), control is performed such that the use of the actuator will be resumed (step S23).

Effect of Fourth Embodiment

As described above, when the temperature sensor itself is configured to generate heat, i.e., when the variable-rigidity member 20, which is a heating element, combines the function of the temperature sensor as with the first embodiment, even if the temperature sensor is overheated, since power supply to the temperature sensor itself is stopped after overheating determination, the endoscope system according to the fourth embodiment achieves the effect of being able to reduce heat dissipation time.

Fifth Embodiment

Next, a fifth embodiment of the present invention will be described.

An endoscope system according to the fifth embodiment is similar to the first embodiment in a basic configuration, and thus only differences will be described here.

Figure 12:
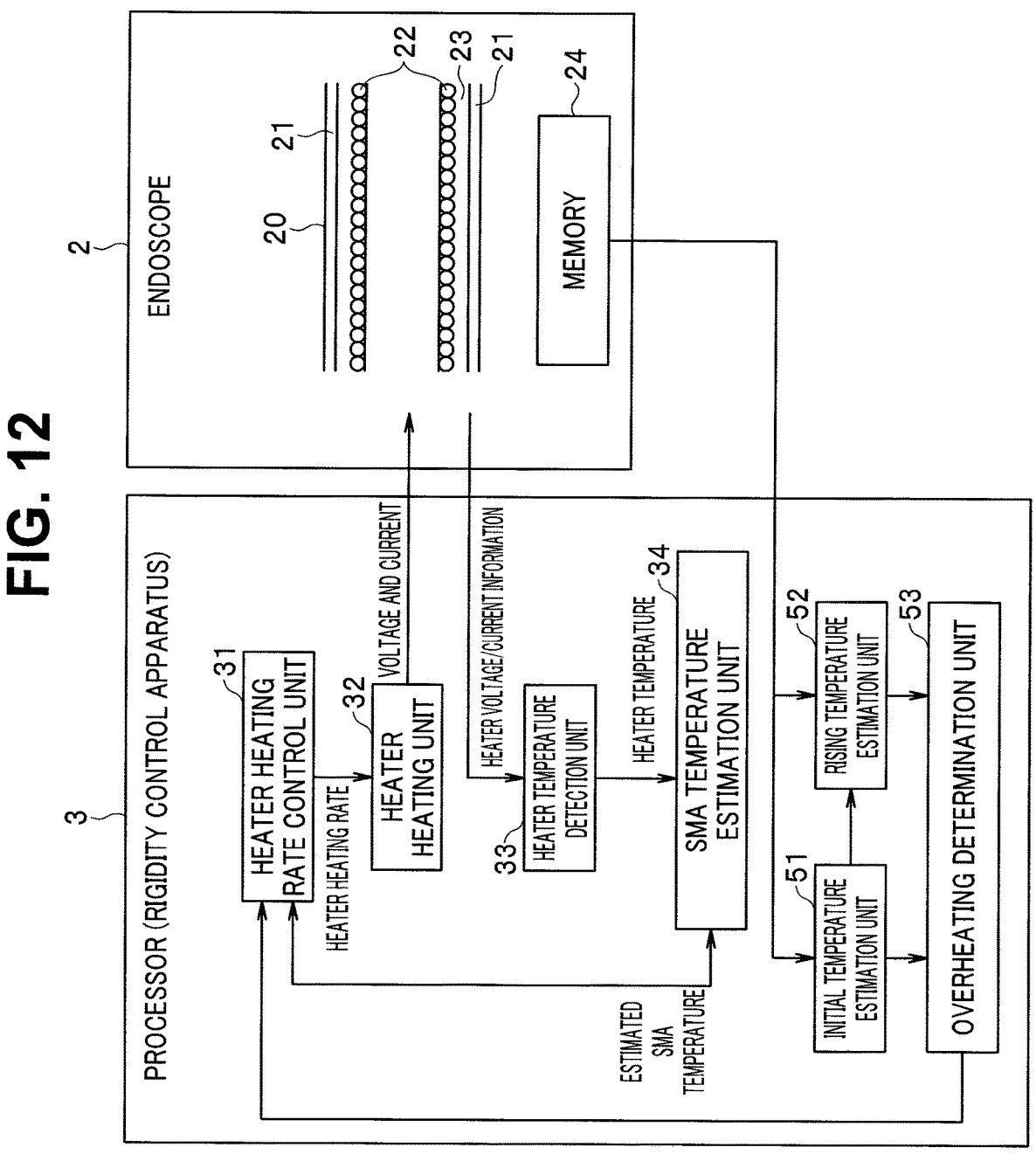
FIG. 12 is a block diagram showing major components of an endoscope and a processor making up an endoscope system according to a fifth embodiment of the present invention.

FIG. 12 is a block diagram showing major components of an endoscope and a processor making up the endoscope system according to the fifth embodiment of the present invention.

The endoscope system according to the fifth embodiment is characterized in that a nonvolatile memory 24 is disposed in the endoscope 2, prestoring various constant parameters for an initial surface temperature estimation unit and a rising temperature estimation unit, where the constant parameters depend on the model or individual of the endoscope 2. According to the present embodiment, when the processor 3 is powered on with an endoscope 2 connected to the processor 3, the processor 3 automatically acquires data unique to the connected endoscope 2 from the nonvolatile memory 24 and uses the acquired data for predetermined arithmetic operations.

Effect of Fifth Embodiment

As described above, the endoscope system according to the fifth embodiment can accommodate differences in heat conduction properties caused by the models or individuals of the endoscopes 2 and estimate endoscope surface temperature with a higher degree of reliability.

The present invention is not limited to the embodiments described above, and various changes and alterations are possible without departing from the gist of the invention.

What is claimed is:

1. A processing apparatus comprising:
a processor comprising hardware, the processor being configured to:
    acquire heating element temperature data from a temperature sensor configured to estimate temperature of a heating element provided in an insertion portion of an endoscope inserted into a subject;
    output initial surface temperature, which is insertion portion surface temperature at a first time point prior to a start of heating of the heating element, based on the heating element temperature data at the first time point,
    estimate changes in the insertion portion surface temperature over time after the first time point based on the heating element temperature data after the first time point using the initial surface temperature as an initial value of the insertion portion surface temperature; and output a change in the insertion portion surface temperature based on a mathematical equation containing a function that has a gain and a time constant or a modification of the function, using the heating element temperature data as an input value to the mathematical equation.

2. The processing apparatus according to claim 1, wherein the processor is configured to determine to stop heating the heating element based on the insertion portion surface temperature.

3. The processing apparatus according to claim 1, wherein the processor is configured to output the initial surface temperature based on the heating element temperature data only at the first time point.

4. The processing apparatus according to claim 1, wherein the processor is configured to:

output the initial surface temperature based on the heating element temperature data only at the first time point; and output a change in the insertion portion surface temperature based on a mathematical equation containing a function that has a gain and a time constant or a modification of the function, using the heating element temperature data as an input value to the mathematical equation.

5. The processing apparatus according to claim 1, wherein the processor is configured to output the initial surface temperature by adding a predetermined safety value.

\* \* \* \* \*